(12) United States Patent
Igci et al.

(10) Patent No.: US 10,105,668 B2
(45) Date of Patent: Oct. 23, 2018

(54) GAS DISTRIBUTION IN OXIDATION REACTIONS

(71) Applicant: ExxonMobil Chemical Patents Inc., Baytown, TX (US)

(72) Inventors: Yesim Igci, Spring, TX (US); Bryan A. Patel, Jersey City, NJ (US); Min Chang, Belmont, CA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/577,030

(22) PCT Filed: Jun. 3, 2016

(86) PCT No.: PCT/US2016/035825
§ 371 (c)(1),
(2) Date: Nov. 27, 2017

(87) PCT Pub. No.: WO2017/003644
PCT Pub. Date: Jan. 5, 2017

(65) Prior Publication Data
US 2018/0141018 A1 May 24, 2018

Related U.S. Application Data

(60) Provisional application No. 62/186,967, filed on Jun. 30, 2015.

(51) Int. Cl.
| | | |
|---|---|---|
| *C07C 407/00* | (2006.01) | |
| *C07C 409/14* | (2006.01) | |
| *B01J 8/00* | (2006.01) | |
| *B01J 8/22* | (2006.01) | |
| *B01J 4/00* | (2006.01) | |

(52) U.S. Cl.
CPC ............... *B01J 8/22* (2013.01); *B01J 4/004* (2013.01); *C07C 407/00* (2013.01); *C07C 409/14* (2013.01); *C07C 2601/14* (2017.05)

(58) Field of Classification Search
CPC ........ C07C 407/00; C07C 409/14; B01J 8/22; B01J 4/004
See application file for complete search history.

(56) References Cited

U.S. PATENT DOCUMENTS

| | | |
|---|---|---|
| 5,439,556 A | 8/1995 | Sethna et al. |
| 6,037,513 A | 3/2000 | Chang et al. |
| 9,586,898 B2 | 3/2017 | Dakka et al. |
| 2004/0241059 A1 | 12/2004 | Seidlitz et al. |
| 2014/0148569 A1 | 5/2014 | Dakka et al. |
| 2014/0336417 A1 | 11/2014 | Patel et al. |
| 2014/0371490 A1 | 12/2014 | Patel et al. |

FOREIGN PATENT DOCUMENTS

| | | |
|---|---|---|
| CN | 1356161 A | 7/2002 |
| CN | 101869819 B | 12/2014 |
| WO | 2012/134549 A | 10/2012 |
| WO | 2014/137623 A | 9/2014 |
| WO | 2017/003643 A | 1/2017 |

OTHER PUBLICATIONS

Kulkarni, A.V., et al., "Design and selection of sparger for bubble column reactor. Part I: Performance of different spargers", Chem Eng'g Research & Design, vol. 89 , pp. 1972-1985, 2011.
Kulkarni, A.V., et al., "Design and selection of sparger for bubble column reactor. Part II: Optimum sparger type and design", Chem Eng'g Research & Design, vol. 89, pp. 1986-1995, 2011.

*Primary Examiner* — Sikarl A Witherspoon

(57) ABSTRACT

Systems, methods, and apparatus for distribution of oxygen-containing gas within a gas-liquid oxidation reaction are provided herein. The invention is particularly suited for oxidation of liquid-phase organic reactants with oxidizing gas, such as the oxidation of cyclohexylbenzene to cyclohexylbenzene hydroperoxide using an oxygen-containing gas. The oxygen-containing gas is distributed through a gas distributor and into a liquid-phase reaction medium within an oxidation reactor. In some aspects, this achieves a high degree of uniformity of oxygen concentration within the liquid-phase reaction medium. The gas distributor is disposed within a lower portion of the reactor, and may comprise a network of conduits in fluid communication with each other, which are arranged within a plane that is substantially parallel to a bottom surface of the reactor. A plurality of orifices are disposed on the conduits, such that oxygen-containing gas flows through the conduits and into the liquid-phase reaction medium via the orifices.

25 Claims, 7 Drawing Sheets

(Plane View)

GAS DISTRIBUTION IN OXIDATION REACTIONS

CROSS REFERENCE TO RELATED APPLICATIONS

This application is a National Phase Application claiming priority to PCT Application Serial No. PCT/US2016/035825 filed Jun. 3, 2016, and U.S. Provisional Application No. 62/186,967 filed Jun. 30, 2015, the disclosures of which are incorporated herein by reference.

FIELD

This disclosure relates to systems, methods, and apparatus for the oxidation of organic compounds, particularly cycloalkylaromatic compounds, to hydroperoxides. In particular, the present invention relates to processes and apparatus for distributing gas feed in the oxidation of organic compounds in liquid phase. The present invention is useful, e.g., in oxidation processes for making cyclohexylbenzene hydroperoxide via the oxidation of cyclohexylbenzene.

BACKGROUND

The production of phenol and/or cyclohexanone from cyclohexylbenzene (CHB) is an emerging technology, interesting in that it co-produces cyclohexanone, rather than acetone. CHB may be produced, for example, by direct alkylation of benzene with cyclohexene, or as disclosed in U.S. Pat. No. 6,037,513, by contacting benzene with hydrogen in the presence of a catalyst. The cyclohexylbenzene may then be oxidized to the corresponding hydroperoxide and the hydroperoxide cleaved to phenol and cyclohexanone using a catalyst. Depending upon need or demand, the phenol and cyclohexanone may each be taken as products, and/or the phenol can be hydrogenated to produce additional cyclohexanone, and/or the cyclohexanone can be dehydrogenated to produce additional phenol. Cyclohexanone is widely used to make caprolactam, which, in turn, is used for making nylon-6, a widely used polymer material. Phenol may be used to make a wide variety of chemical products, including bis-phenol A, polycarbontaes, phenolic resins, and the like.

In such processes for the co-production of phenol and cyclohexanone, the oxidation of CHB to cyclohexylbenzene-hydroperoxide (CHB-HP) may be a gas-liquid oxidation that takes place through a free radical chain reaction homogeneously catalyzed by an N-hydroxy-substituted cyclic imide, such as N-hydroxyphthalimide (NHPI), for instance as described in WO 2014/137623. In particular, the liquid-phase reaction medium comprising the CHB is contacted with an oxygen-containing gas (e.g., air or $O_2$) to form the CHB-HP. Desirably, the oxidation is conducted at low per-pass conversion to optimize process yields, because the desired CHB-HP product is a reaction intermediate. One way to achieve this result is through a shorter residence time of the reactants, ensuring that only a small portion of the gas-phase oxygen reacts with the liquid-phase CHB. However, such a process entails a large degree of oxygen bypass (e.g., un-used oxygen passing through the liquid-phase reaction medium). This problem can be compounded because the kinetics of the gas-liquid oxidation of CHB to CHB-HP are relatively slow, which means that highly concentrated zones of oxygen-containing gas within the liquid-phase reaction medium may form and pass unreacted through the liquid-phase reaction medium, only to collect in the vapor-phase overhead in the reactor. Such excessive oxygen bypass will lead to quickly rising oxygen concentration in the headspace, which will result in dangerous flammable conditions if not controlled. Therefore, a sufficient amount of oxygen must be supplied to the liquid phase reaction medium in order to maintain the desired conversion rate, while at the same time, delivery of the oxygen-containing gas must be carried out so as to maintain the oxygen concentration in the vapor phase headspace of the reactor below the flammability limit for safe operation.

One option is a lower gas flow rate into the reactor. However, this reduces the speed at which cycloalkylaromatic feed is converted to the desired cycloalkylaromatic hydroperoxide, which negatively impacts the process economics. Therefore, a better solution is desired.

The present inventors have discovered a means to maintain the desired per pass conversion and speed of conversion, while minimizing the amount of oxygen that will be present in the reactor headspace, thereby allowing for safe operation of the oxidation reactor below the overhead oxygen concentration flammability limit. In particular, a gas distributor of the particular designs according to various embodiments described herein maximizes the distribution of vapor phase oxygen-containing gas through the liquid phase reaction medium, thereby maximizing efficiency of the reaction and minimizing gas bypass through the liquid phase reaction medium and into the reactor headspace. In addition, liquid distributors instead of or in addition to such gas distributors in yet further embodiments of the invention described herein may further enhance the mixing of reactants through the liquid phase reaction medium.

Further, although described in the context of CHB oxidation to CHB-HP, it is believed that the presently disclosed invention may be equally applicable to the oxidation of any liquid-phase organic reactant using an oxygen-containing gas, particularly oxidation reactions featuring relatively slow reaction kinetics and requiring carefully controlled per-pass conversion.

Although oxidation of CHB to CHB-HP via N-hydroxy-substituted cyclic imides has been disclosed, the inventors are not aware of any prior published recognition of the problem of gas bypass (let alone a solution to such problem) in such a reaction on an industrial scale, nor are the inventors aware of any current commercial practice of such oxidation reactions on an industrial scale. Some references of interest may include: Kulkarni, A. V. & Joshi, J. B., *Design and selection of sparger for bubble column reactor. Part I: Performance of different spargers*, CHEM ENG'G RESEARCH & DESIGN 89 (2011), 1972-1985; Kulkarni, A. V., Joshi J. B., *Design and selection of sparger for bubble column reactor. Part II: Optimum sparger type and design*, CHEM ENG'G RESEARCH & DESIGN 89 (2011): 1986-1995; US Patent Application Publication Nos. 2014/0148569, 2014/0336417, 2014/0371490; and WIPO patent publication WO 2014/137623.

SUMMARY

The present invention provides for systems, methods, and apparatus for distributing an oxygen-containing gas, which achieves a high degree of uniformity in the distribution of the gas through a liquid-phase reaction medium in the gas-liquid oxidation reaction of liquid-phase organic compounds with oxygen-containing gas, such as the oxidation of liquid-phase cycloalkylaromatic compounds to cycloalkylaromatic hydroperoxides using an oxygen-containing gas (e.g., air, $O_2$, $O_2/N_2$ mixtures, and the like). Such a distribution allows for reasonable flow rates of the oxidizing gas into the liquid-phase reaction medium to be maintained, while ensuring minimal gas bypass, thereby minimizing the buildup of oxygen concentration in the reactor overhead. This helps maintain oxygen overhead concentration at safe levels (such as less than or equal to 8 vol % oxygen in the vapor-phase overhead), below the flammability limit, without excessively slowing the gas feed rate (and therefore slowing the rate of reaction).

In some aspects, the present invention provides a gas distributor, and methods involving the use of such a distributor, to accomplish this gas distribution into the liquid-phase reaction medium within an oxidation reactor. Gas distributors according to some embodiments are disposed in a lower portion of the oxidation reactor. Such distributors comprise a network of conduits in direct or indirect fluid communication with one another, and having a plurality of orifices disposed thereon, such that oxygen-containing gas flows through the conduits and out into the liquid-phase reaction medium via the orifices. The network of conduits according to some aspects is disposed within a gas distributor horizontal cross-sectional area, which lies in a plane substantially parallel to a bottom surface of the oxidation reactor, and which further occupies an area that is from 70 to 95% of the cross-sectional area of the portion of the reactor in which the distributor is disposed. The density of the orifices, or holes, disposed upon the conduits is on average 0.5 to 5 orifices per square foot within the gas distributor horizontal cross-sectional area.

The gas distributor may have any one of a number of arrangements, although gas distributors according to some embodiments are arranged as arm distributor networks, comprising one or more header conduits in fluid communication with 10 to 50 arm conduits running transverse to, and intersecting, the header conduit(s). Other arrangements are also contemplated, including concentric ring spargers and perforated plate spargers, among others.

Some embodiments provide a single oxidation reactor comprising a gas distributor according to any of the above-described aspects. Other embodiments provide a system of two or more oxidation reactors, any one or more of which may comprise such a gas distributor. Systems according to particular aspects include three oxidation reactors in series, each with progressively larger diameters. Parallel reactor systems are also contemplated in other aspects. In yet further embodiments, any one or more of the reactors also comprises a liquid distributor for distributing liquid feed and/or recycled reaction medium into the reactor to form the liquid phase reaction medium. According to some aspects, the liquid distributor may be disposed in a lower portion of the oxidation reactor, such that the liquid distributor is located, in part or in whole, either above or below the gas distributor. In certain aspects, the liquid distributor is at least partly located above the gas distributor.

The oxidation reactors or reactor systems with gas distributors may be suitable for any gas-liquid oxidation of a liquid-phase oxidizable organic compound. Particularly contemplated in some embodiments is the oxidation of a liquid phase oxidation reaction mixture comprising cyclohexylbenzene, so as to yield cyclohexylbenzene-hydroperoxide. This oxidation may further be incorporated as part of a larger process to produce cyclohexanone and/or phenol from benzene.

DETAILED DESCRIPTION OF THE EMBODIMENTS

Figure 1:
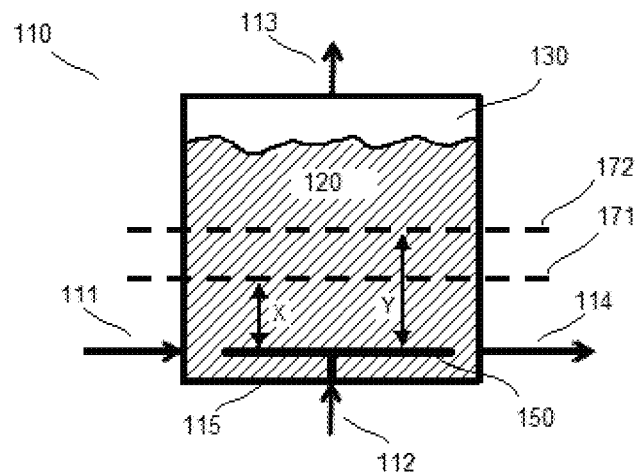
FIG. 1 is a simplified diagram illustrating a side view of operation of an oxidation reactor in accordance with some aspects of the present invention.

The present invention provides for gas-liquid oxidation of organic compounds in the liquid phase using a gas distributor (which may also be referred to as a sparger) designed to distribute an oxygen-containing gas through the liquid-phase reaction medium so as to achieve relatively uniform distribution of the gas through a given cross-section of the liquid-phase reaction medium. Preferably, the relatively uniform distribution of the gas helps maintain high efficiency in the oxidation reaction, maximizing utilization of the oxygen (and thereby minimizing its bypass).

The systems, methods, and apparatus provided herein are particularly suited for gas-liquid oxidation of organic compounds having relatively slow reaction kinetics, and/or gas-liquid oxidation reactions in which per-pass conversion is desirably low (e.g., less than 50% conversion of the species to be oxidized). A particular example of such a reaction, as noted above and also as described in greater detail below, is the oxidation of cyclohexylbenzene to cyclohexylbenzene-hydroperoxide.

Furthermore, such an oxidation reaction (and systems and apparatus for carrying out such a reaction) may, according to some embodiments, form an integral part of a larger overall process for the co-production of cyclohexanone and phenol from cyclohexylbenzene produced by the alkylation or hydroalkylation of benzene. Such processes, in general, include the alkylation or hydroalkylation of benzene to form cyclohexylbenzene, which in turn is oxidized to cyclohexylbenzene-hydroperoxide according to the example reaction detailed herein. The cyclohexylbenzene-hydroperoxide is then cleaved (e.g., using an acid catalyst) to form the desired cyclohexanone and phenol products. These antecedent and subsequent processes surrounding the oxidation reaction in such embodiments are described in greater detail following the below description of the oxidation reaction.

Oxidation of Cyclohexylbenzene

In the oxidation of cyclohexylbenzene, cyclohexylbenzene is converted to cyclohexyl-1-phenyl-1-hydroperoxide, otherwise referred to herein as cyclohexylbenzene-hydroperoxide (CHB-HP), the desired hydroperoxide, according to the following Reaction-3:

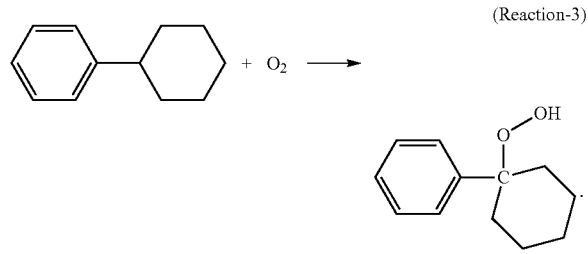
(Reaction-3)

The reaction is preferably carried out as a gas-liquid reaction, with the cyclohexylbenzene in the liquid phase being contacted by an oxygen-containing gas. This may be accomplished, e.g., by passing the oxygen-containing gas through the liquid-phase reaction medium comprising the cyclohexylbenzene (for instance, as in a bubble column reactor).

However, the desired hydroperoxide may further react, producing undesired byproducts such as phenylcyclohexanols, hydroperoxy hexaphenones, and others. As such, it is preferable to operate the reaction at a relatively low conversion per pass, such as a conversion of about 5 to about 30 mol % per pass, for instance about 5 to any one of about 7, 8, 9, 10, 11, 12, 13, 14, or 15 mol % per pass. In some embodiments, multiple series reactions may be used. For instance, two, three, four, five or more series reactors may be used, each operating at a per-pass conversion within one of the aforementioned ranges, thereby increasing the overall conversion. Overall conversion may be about 10 to about 50 mol %, such as an overall conversion ranging from a low of any one of about 10, 15, 16, 17, 18, 19, 20, 21, 22, 23, 24, and 25 mol % to a high of any one of about 25, 26, 27, 28, 29, 30, 35, 40, 45, and 50 mol %, provided the high is greater than the low end of the range. In particular embodiments, per-pass conversion may be about 7-10 mol % (such as about 8-9 mol %) in each of one, two, or three series reactors (thereby providing an overall conversion of about 21-30 mol % (such as about 24-27 mol %) when three series reactors are used).

In addition, the reaction kinetics for the desired reaction are relatively slow. Therefore, the under-utilization of oxygen within the oxygen-containing gas is a real possibility, which, if not properly managed, could lead to significant oxygen bypass as the oxygen-containing gas is passed through the liquid-phase reaction medium. This will lead to build-up in oxygen concentration in the vapor phase overhead, causing a combustion risk. One of the aims of the present invention is to provide adequate distribution of the oxygen-containing gas through the liquid-phase reaction medium so as to maximize the efficiency of consumption of oxygen in the gas, thereby minimizing bypass (which, in turn, helps maintain the oxygen concentration in the reactor overhead at safe levels).

Oxidation according to some exemplary processes will now be described with reference to FIG. 1. According to the general process of some embodiments depicted in FIG. 1, a liquid feed stream 111 comprising cyclohexylbenzene is provided to an oxidation reactor 110 so as to form a liquid-phase reaction medium 120 (comprising the cyclohexylbenzene) in the oxidation reactor 110. An oxidation catalyst is preferably supplied to the liquid phase reaction medium, either with the feed or separately from the feed. The oxidation catalyst may be an N-hydroxy-substituted cyclic imide, such as any of the oxidation catalysts described in Paragraphs [0050]-[0054] of WIPO Publication WO 2014/137623. A particularly suitable catalyst is N-hydroxyphthalimide (NHPI). Optionally, the liquid feed may be provided to the oxidation reactor through a liquid distributor (not shown in FIG. 1), discussed in greater detail hereinbelow.

Oxidation further includes contacting the liquid-phase reaction medium 120 with an oxygen-containing gas, such as air and various derivatives of air, in the reactor 110. For example, a stream of pure $O_2$, $O_2$ diluted by inert gas such as $N_2$, pure air, or other $O_2$-containing mixtures can be introduced into the reactor as a gas inlet stream 112. The gas is introduced through one or more inlets into a gas distributor 150 disposed in the oxidation reactor 110 (and which becomes submerged within the liquid-phase reaction medium 120 as the feed stream 111 is provided to the reactor 110). The gas passes through the gas distributor 150 and exits into the liquid-phase reaction medium 120, whereupon it will bubble up through the reaction medium 120 and into the vapor-phase overhead 130 of the reactor. The gas may be drawn off as a gas outlet stream 113. As oxygen within the gas contacts the liquid-phase reaction medium 120, the desired cyclohexylbenzene-hydroperoxide is formed in the reaction medium 120, and the liquid phase may thereafter be drawn off from the reactor 110, e.g., via liquid outlet stream 114. The liquid inlet stream 111 may be delivered to the reactor 110 via a liquid inlet disposed at any height along the reactor; similarly, the liquid outlet stream 114 may be drawn from the reactor 110 via a gas outlet at any height along the reactor. The locations of such streams shown in FIG. 1 are not intended to be limiting. Similarly, the gas inlet stream 112 may be delivered to the reactor 110 via one or more gas inlets disposed alongside the reactor at any height, so long as it is delivered into the reaction medium 120 by way of the gas distributor 150 (i.e., such that the gas distributor 150 is in fluid communication with the one or more gas inlets). Furthermore, at least a portion of the liquid outlet stream 114 and/or the gas outlet stream 113 may be recycled to the reactor 110, either via separate liquid/gas inlets or by combination with the liquid inlet stream 111 and gas inlet stream 112, respectively, so long as any such recycled gas is delivered through the gas distributor 150.

Desired Oxygen Distribution and Concentration

Preferably, the gas is distributed into the liquid-phase reaction medium 120 such that in any given continuous area of 10.0 centimeters by 10.0 centimeters inside (i) a first horizontal cross-section 171 of the liquid-phase reaction medium 120, and/or (ii) a second horizontal cross-section 172 of the liquid-phase reaction medium 120, the average quantity of oxygen passing through the given continuous area per second (QO1) is in a range from 60% to 140% of QO2, where QO2 is the average quantity of oxygen passing through the whole given horizontal cross-section, expressed in terms of quantity of oxygen per 100 square centimeters per second. Even more preferably, QO1 is in a range from 80% to 120% of QO2.

Furthermore, the gas in some embodiments is distributed such that the oxygen concentration $[O_2]$ at either or both of the horizontal cross sections 171 and 172 is greater than a threshold oxygen concentration $[O_2^*]$ throughout the reaction medium (that is, such that $[O_2]/[O_2^*]>1$). The threshold oxygen concentration is the localized concentration of oxygen in the liquid phase above which the reaction becomes independent of oxygen concentration (i.e., such that oxygen concentration is no longer a bottleneck to the rate and/or extent of reaction). The threshold oxygen concentration depends upon temperature and oxidation catalyst (e.g., NHPI) concentration. The threshold oxidation concentration will also depend upon the particular liquid-phase oxidation reaction taking place. Threshold oxygen concentration may be readily determined for any given temperature and oxidation catalyst concentration by studying reaction rates for varying oxygen concentrations, and determining the concentration above which no change in reaction rate occurs.

Each horizontal cross section 171 and 172 is, respectively, a cross-sectional area in a horizontal plane (as shown in FIG. 1, each horizontal plane is substantially parallel to the bottom 115 of the reactor 110); as such, each cross section 171 and 172 is illustrated as a dashed line in the side-on view of the reactor 110 in FIG. 1. As used herein, "substantially parallel" in reference to another plane, vector, line, conduit, component, or the like, means +/−10° (with 0° being exactly parallel). Further, a "horizontal" plane, component, or cross section is one that is substantially parallel (i.e., +/−10°) with respect to the normal of the gravity acceleration vector where the reactor 110 is located. As shown in FIG. 1, the first horizontal cross section 171 is X centimeters above the top of the gas distributor 150, while the second horizontal cross section 172 is Y centimeters above the top of the gas distributor 150 (where Y>X). Note that FIG. 1 is not drawn to scale, but merely used to illustrate the relationship between the various elements discussed herein.

In various embodiments, X may be less than or equal to any one of 5, 10, 15, 20, 25, 50, 75, and 100 centimeters (i.e., such that the first horizontal cross section 171 is less than or equal to 5, 10, 15, 20, 25, 50, 75, and 100 centimeters above the top of the gas distributor 150). In various embodiments, Y may be greater than or equal to any one of 100, 200, 300, 400, 500, and 600 centimeters, provided that Y is greater than X.

The relatively uniform distribution of oxygen through a given cross-section of the liquid-phase reaction medium 120 described by these embodiments enables highly efficient utilization of the oxygen within the oxygen-containing gas passing through the liquid-phase reaction medium 120, which helps minimize the amount of oxygen bypass, thereby resulting in adequately low concentration of oxygen in the vapor-phase overhead 130. This is so despite the desirably low per-pass conversion in the reaction, and the slow reaction kinetics.

Distributing the oxygen-containing gas in some embodiments maintains the overhead oxygen concentration at safe levels well below the flammability limit of 10.5 vol %. Preferably, the oxygen concentration in the overhead vapor phase is maintained at or below 8.5 vol %, such as at or below 8.0 vol %, even more preferably at or below 5.0 vol %.

Gas Distributor

In some embodiments, the gas distributor through which the oxygen-containing gas is delivered into the liquid-phase reaction medium has one or more particular features. In certain embodiments, the aforementioned relatively uniform distribution of oxygen gas in the reaction medium is achieved through the use of a gas distributor according to such embodiments.

A gas distributor according to some embodiments is disposed within a lower portion of the oxidation reactor. As used herein, a "lower portion" of the oxidation reactor refers to the bottom ¼ of the reactor. That is, for a reactor of dispersed liquid height H meters, the "lower portion" of the reactor encompasses the volume within the reactor from the bottom of the reactor to a plane parallel to the reactor bottom, which is located 0.25*H meters above the bottom of the reactor. As used herein, reference to the gas distributor being "disposed in" the reactor at a given height (or range of heights) indicates the distance between (1) the reactor bottom and (2) the bottom-most portion of the gas distributor. For instance, where some components of the gas distributor are disposed lower in the reactor than other components, the lowest components are used for measurement of height at which the gas distributor is disposed.

In particular embodiments, where dispersed liquid height in the reactor during normal operation is about 0.1 ft to about 50 ft (about 0.03 to about 15.24 m), the gas distributor may be disposed within the reactor such that it is elevated about 0.01 to about 3.81 m from the bottom of the reactor. In some embodiments, dispersed liquid height may be 0.1 ft to any one of about 10, 12, 15, 17, 20, 22, and 25 ft (0.03 m to any one of about 3.05, 3.66, 4.57, 5.18, 6.10, 6.71, and 7.62 m). The cost of gas compression may be a driving factor to maintaining relatively low dispersed liquid height in such embodiments. However, in yet other embodiments, dispersed liquid height may range from about 15 to 35 ft (about 4.57 to 10.67 m), such as about 15 to 25 ft (about 4.57 to about 7.62 m), since each foot of liquid height allows more liquid to fit in a single reactor (thereby allowing a reactor of equal diameter to hold more liquid phase reaction medium, and therefore provide a greater amount of product per pass). In addition, maintaining adequate height according to such embodiments may help maintain circulation of reactants within the liquid phase reaction medium. In general, from the top of the dispersed liquid height during normal operation (i.e., from the top of the liquid-phase reaction medium) to the top of the reactor, a space is reserved for collecting residual gas exiting the reaction medium as vapor phase overhead. The residual gas in the vapor phase overhead will have an $O_2$ partial pressure lower than in the gas supplied to the reaction medium through the gas distributor.

Figure 2:
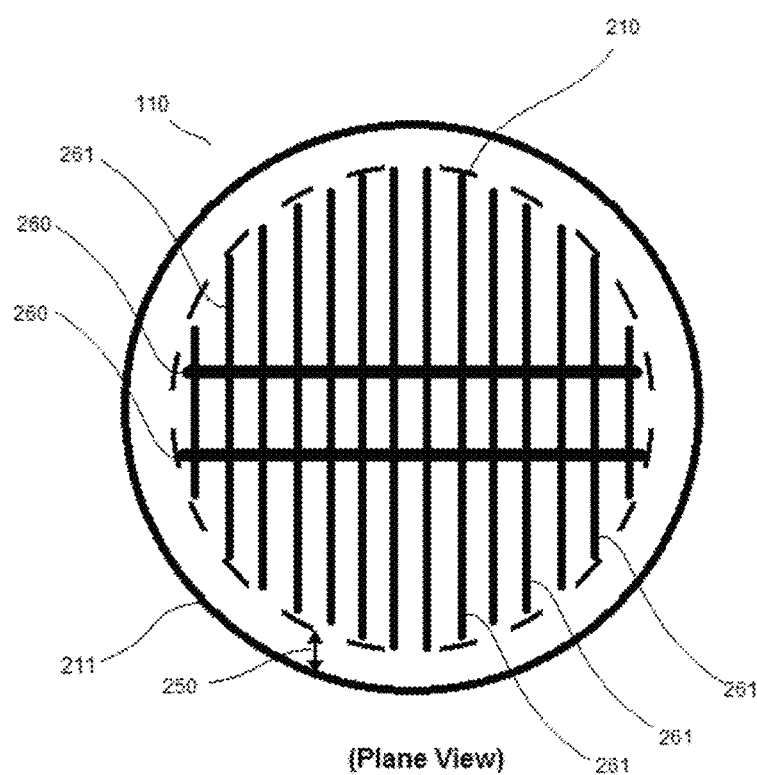
FIG. 2 is a plane view of a gas distributor disposed within an oxidation reactor, in accordance with some aspects of the present invention.

With reference to the example gas distributor according to some embodiments that is illustrated in FIG. 2 (showing a plan view of an arm-and-header type gas distributor), the gas distributor 150 typically comprises a network of conduits into which the oxygen-containing gas is delivered via one or more inlets (not shown in FIG. 2), and through which the oxygen-containing gas may flow. As shown in FIG. 2, the network of conduits comprises header conduits 260 and arm conduits 261. Preferably, the one or more inlets for the oxygen-containing gas are in direct fluid communication with at least the header conduits, where such conduits are present. In some preferred embodiments, all of the conduits are in direct or indirect fluid communication with one another, such that the oxygen-containing gas is distributed throughout the entire network of conduits. The network of conduits may be disposed within a horizontal plane such that the center lines of the conduits are substantially within said horizontal plane. The smallest possible area within this plane that may be defined so as to encompass the network of conduits is considered the "gas distributor horizontal cross-sectional area" 210. A plurality of orifices (not shown in FIG. 2) is disposed along the conduits and within the distributor horizontal cross-sectional area 210. Preferably, the distributor horizontal cross-sectional area is from 70 to 95% of the cross-sectional area of the lower portion of the oxidation reactor in which the gas distributor is disposed (that is, the cross-sectional area of the reactor in a plane, or top-down, view). This may be referred to as 70 to 95% "gas distributor coverage." Put in mathematical terms, where the reactor has inner cross-sectional area A square meters in the plane in which the gas distributor is disposed, the gas distributor cross-sectional area is preferably 0.7 Å m² to 0.95 Å m². More preferably, the gas distributor coverage is about 75% to about 95% of the cross-sectional area of the lower portion of the oxidation reactor in which the gas distributor is disposed, such as about 75% to any one of 80%, 85%, 90%, and 95%; or about 80% to any one of about 85% and 90%.

In particular embodiments, the reactor 110 may have a circular cross-sectional area along the plane in which the gas distributor is disposed, as illustrated in FIG. 2. A reactor according to such embodiments may be a cylindrical reactor with diameter D. In the discussion herein, the term "cylinder" has the modern mathematical definition of the term. The term cylinder should not be limited strictly to the special case of a cylinder with a circular cross-section. Instead, a cylinder can refer to any shape defined by translating a closed, continuous two-dimensional cross-section along an axis in a parallel manner. Thus, in addition using a circular cross-section to form a circular cylinder, other cross-sectional shapes can be used, such as parallelepipeds, trapezoids, hexagons, triangles, and/or other regular or irregular shapes with an arbitrary number of sides and/or curved portions. Where the cross-sectional shape is a circle or regular polygon (according to the geometrical definition of regular), it may have a diameter D taken as a straight line passing from one side of the cross-section to the other, through the center of the cross-section. Reactors according to such embodiments may have diameter D ranging from 2 ft to 200 ft (about 0.61 m to about 60.96 m). More particularly, reactors in various embodiments may have diameter D ranging from a low of any one of about 2, 5, 10, 15, 20, 25, 30, 35, 40, 45, 50, 55, 60, 65, 70, 75, 80, and 85 feet (about 0.61, 1.52, 3.045, 4.57, 6.10, 7.62, 9.14, 10.67, 12.19, 13.72, 15.24, 16.76, 18.29, 19.81, 21.34, 22.86, 24.38, and 25.91 meters, respectively), to a high of any one of about 40, 45, 50, 55, 60, 65, 70, 75, 80, 85, 90, 95, 100, 105, 110, 115, and 120 feet (about 12.19, 13.72, 15.24, 16.76, 18.29, 19.81, 21.34, 22.86, 24.38, 25.91, 27.43, 28.95, 30.48, 32.00, 33.53, 35.05, and 36.58 meters, respectively), provided that the high end of the range is greater than the low end.

Where the reactor is cylindrical about an axis according to such embodiments, the gas distributor horizontal cross-sectional area is preferably centered about the same axis, as illustrated in FIG. 2, such that the space 250 between the inner surface of the reactor wall 211 and the outer edge of the gas distributor horizontal cross-sectional area is roughly equal along the entire interior surface of the reactor wall. "Roughly equal" allows for deviations, at any given position, of up to 5% of the average distance between reactor side wall and outer edge of the gas distributor horizontal cross-sectional area.

The conduits of the gas distributor may have inner diameter within a range from a low of any one of about 0.01, 0.02, 0.03, 0.04, 0.05, 0.06, 0.07, 0.08, 0.09, and 0.10 m, to a high of any one of about 0.06, 0.07, 0.08, 0.09, 0.10, 0.15, 0.20, 0.25, 0.30, 0.35, 0.40, 0.45, 0.50, 0.60, 0.70, 0.80, 0.90, and 1.0 m. In some embodiments, the conduits have approximately equal (+/−5% from average) diameters. In yet other embodiments, the conduits may have varying diameter. In certain embodiments, there may be conduits of at least 2, 3, 4, 5, or more different diameters in the network of conduits forming the gas distributor. For instance, as shown in FIG. 2 (and discussed in greater detail below), arm-and-header type gas distributors according to some embodiments may comprise header conduits 260, having diameter $D_1$, and arm conduits 261, having different diameter $D_2$, representing an embodiment with conduits of 2 different diameters. The header diameter $D_1$ of such embodiments may be at least 2, 3, 4, or 5 times greater than the arm diameter.

With respect to the orifices disposed along the conduits, in some embodiments, there are on average 0.1 to 10 of the orifices per square foot (about 1.076 to 107.6 orifices per m²) within the gas distributor horizontal cross-sectional area. Preferably, there are on average 0.5 to 5 orifices per square foot (5.38 to 53.8 orifices per m²); more preferably on average about 1 to 3 orifices per square foot (about 10.76 to about 32.29 orifices per m²), such as about 2 orifices per square foot (21.53 per m²). The qualifier "on average" indicates that the orifices in such embodiments are not necessarily distributed evenly within the distributor horizontal cross-sectional area. However, in some embodiments, the orifices are evenly distributed within the gas distributor horizontal cross-sectional area (meaning that the spacing between any two orifices is approximately equal to the spacing between any other two orifices). In such embodiments, the spacing between each orifice is about 0.05 to about 0.25 m. For instance, the spacing between each orifice may range from a low of any one of about 0.05, 0.06, 0.07, 0.08, 0.09, 0.1, 0.11, 0.12, 0.13, and 0.14 m to a high of any one of about 0.10, 0.11, 0.12, 0.13, 0.14, 0.15, 0.16, 0.17, 0.18, 0.19, 0.20, and 0.25 m, provided the high end of the range is greater than the low end. For example, the spacing between any two orifices may be about 0.10 m to about 0.20 m, such as about 0.12 to about 0.18 m, or 0.14 m to about 0.19 m, and so on.

Further, the gas distributor may contain any number of drainage holes through which any liquid material can flow out of the distributor conduits due to gravity in case emptying the reactor body and/or the distributor conduits is needed. These drainage holes, where present, are in addition to, and not numbered as part of, the orifices.

Each orifice may have a diameter of about 2 mm to about 10 mm. In some embodiments, orifice diameter may be determined with respect to a desired size for bubbles of the oxygen-containing gas to be released into the liquid-phase reaction medium 120. In certain embodiments, orifice diameter may range from a low of any one of about 1, 2, 3, 4, and 5 mm, to a high of any one of about 3, 4, 5, 6, 7, 8, 9, 10, 11, 12, 13, 14, and 15 mm, provided the high end of the range is greater than the low end. For non-circular orifices, diameter may be approximated as the average distance between pairs of edge points along the orifice, the pairs of edge points joined by a line that intersects the center of the orifice.

Figure 3:
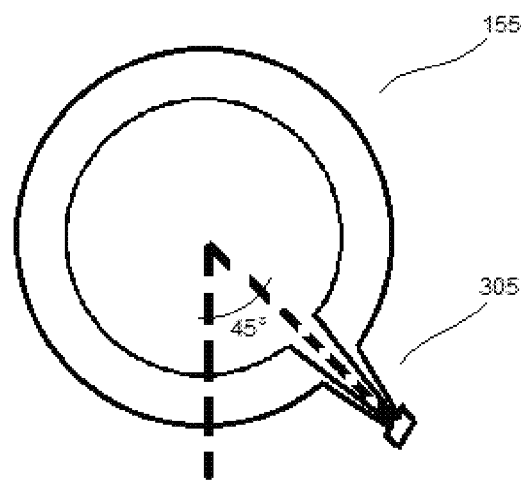
FIG. 3 is a side-on cross-sectional view of a conduit with a nozzle in accordance with some aspects of the present invention.

The orifices may be any opening disposed along the conduits through which the oxygen-containing gas can flow into the liquid-phase reaction medium. In particular embodiments, the orifices are nozzles. The nozzles of such embodiments may optionally extend outward from the conduit, such as shown with respect to the nozzle 305 in FIG. 3, extending away from a conduit (shown as a head-on cross-section of an arm conduit 261 in FIG. 3). The nozzles of such embodiments may further have a particular orientation. In general, the nozzles may be oriented at any angle between −90° and +90° (where 90° is in the plane of the gas distributor horizontal cross-sectional area). Thus, in general, each nozzle may be oriented such that the oxygen-containing gas is expelled from the nozzle in (i) a direction within the plane of the distributor horizontal cross sectional area, (ii) a direction perpendicular to the distributor horizontal cross sectional area and toward a bottom of the oxidation reactor, or (iii) a direction at any angle therebetween. In certain embodiments, the nozzles may be oriented at least partially downward (that is, toward a bottom surface of the reactor). For instance, the nozzle may be oriented so as to expel gas downward at an angle between −60° and +60°, where 0° is a normal vector directed at the reactor bottom surface (and may also be taken as a direction perpendicular to the plane of the gas distributor horizontal cross-sectional area). Preferably, the nozzle is oriented so as to expel gas at an angle between −50° and +50°; more preferably, about 40° to about 50° (or about −50° to about −40°). In some embodiments, as illustrated in FIG. 3, the nozzles 305 are oriented at about 45° (or −45°) relative to the 0° vector directed into the reactor bottom. Preferably, the oxygen-containing gas, after being passed through the nozzles (or other orifices), contacts a bottom surface of the oxidation reactor at least in part, and thereafter rises upward through the liquid phase reaction medium as a plurality of bubbles.

The gas distributor may be operated within a desired range of pressure drops across the network of conduits. In particular, the pressure drop from the gas inlet or inlets in fluid communication with the conduit network to the orifices through which the gas is dispersed into the liquid phase reaction medium may range from a low of any one of about 2, 3, 4, 5, 6, 7, 8, 9, and 10 kPa to a high of any one of about 8, 9, 10, 11, 12, 13, 14, 15, 16, 17, 18, 19, and 20 kPa, provided the high end of the range is greater than the low end. For instance, then, pressure drop during operation may be within the range of from about 4 to about 12 kPa, from about 4 to about 19 kPa, from about 5 to about 20 kPa, etc.

Any of various arrangements of the gas distributor's network of conduits may be used to provide the necessary features (e.g., nozzles per m$^2$, coverage of the gas distributor cross-sectional area, and the like). One preferred arrangement is an arm distributor network, comprising a plurality of arm conduits coupled to one or more header conduits, such as shown in FIG. 2. In particular, the arm distributor network of FIG. 2 comprises two header conduits 260, each in fluid communication with a plurality of arm conduits 261 extending outwardly away from the headers across the gas distributor cross-sectional area 210. In some embodiments, the arm conduits are disposed substantially perpendicularly with respect to the header conduits within the plane of the gas distributor cross-sectional area, as shown in FIG. 2. As used in this context, "substantially perpendicularly" means at an angle from 80° to 100° with respect to another conduit, plane, line, component, or the like (with 90° being exactly perpendicular to, i.e., at a right angle to). According to other embodiments, the arm conduits 261 may run in any non-parallel direction transverse to the header conduits 260 (e.g., at an angle from about 5° to about 175°, such as 45° to 135°, to the header conduit 260, with 0° measured along the direction in which the header conduit 260 runs within the plane of the gas distributor horizontal cross-sectional area 210). The header conduits may run parallel to each other. Further, the arm conduits may each run parallel to each other. However, in embodiments wherein the header conduits do not run parallel to each other, any two or more header conduits may intersect at a junction such that they are in fluid communication with one another. Likewise, where arm conduits do not run parallel to each other, any two or more arm conduits may intersect at one or more junctions such that they are in fluid communication with one another.

Preferably, however, the arm conduits run parallel to one another, and the header conduits likewise run parallel to one another. In such embodiments, the arm conduits may be equally spaced apart from one another, such that each arm conduit runs a distance L from, and parallel to, each of the 2 nearest arm distributors (as indicated in FIG. 2).

Figure 4:
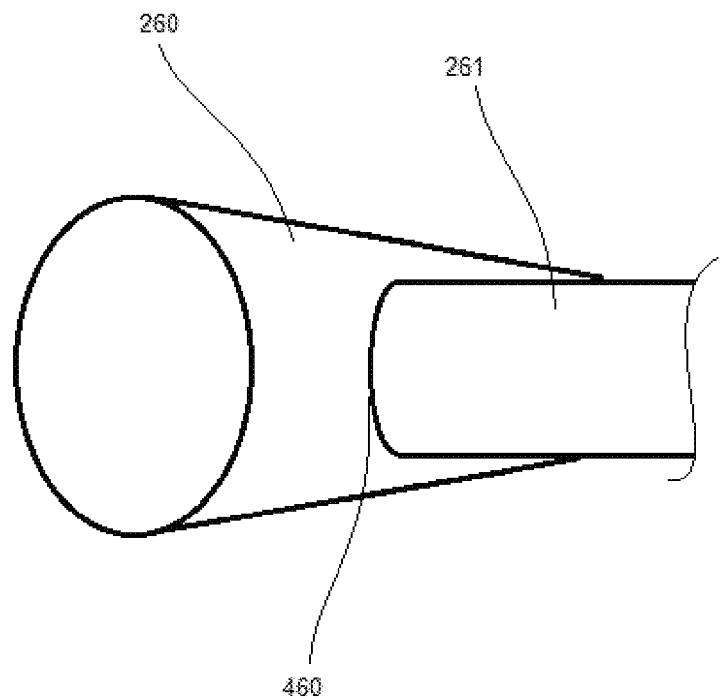
FIG. 4 is a diagram of a junction of conduits within a gas distributor in accordance with some aspects of the present invention.

Further, in a network of arm distributors according to some embodiments, the inner diameter of the header conduits 260 is greater than the inner diameter of the arm conduits 261. Where the header conduit 260 inner diameter is greater than the arm conduit 261 inner diameter, preferably the arm conduits 261 are joined with the header conduit(s) 260 in a manner such that the arm conduits 261 are each centered on the header conduit(s) 260 at junctions 460, such that the header conduit(s) 260 extend farther down in the reactor, as shown in FIG. 4. In such instances, the elevation of the gas distributor is taken as the distance from the reactor bottom to the bottom of the header conduit(s) 260.

In some embodiments, the gas distributor comprises 1, 2, 3, 4, or 5 header conduits. Further, the gas distributor may comprise a number of arm conduits ranging from a low of any one of 10, 11, 12, 13, 14, 15, 16, 17, 18, 19, and 20 arm conduits, to a high of any one of 15, 16, 17, 18, 19, 20, 25, 30, 35, 40, 45, and 50 arm conduits, provided the high end of the range is greater than the low end of the range. For instance, the gas distributor of some embodiments may comprise 2 header conduits, each in fluid communication with a plurality of arm conduits, said plurality of arm conduits comprising from 10 to 45, such as 15 to 25, such as 23, arm conduits, said arm conduits intersecting, and in fluid communication with, both header conduits.

Any other arrangement of the network of conduits may provide the desired features of the gas distributor (e.g., one or more of coverage; orifice size, spacing, and amounts; conduit diameters; gas distributor elevation in the reactor; etc.). Other suitable arrangements include, but are not necessarily limited to, concentric ring spargers, porous plate spargers, membrane spargers, perforated plate distributors, perforated pipes, and the like. In general, any gas distributor arrangement suitable for use in a bubble column may be utilized to provide the necessary features.

Oxidation Reactor Systems

Figure 5:
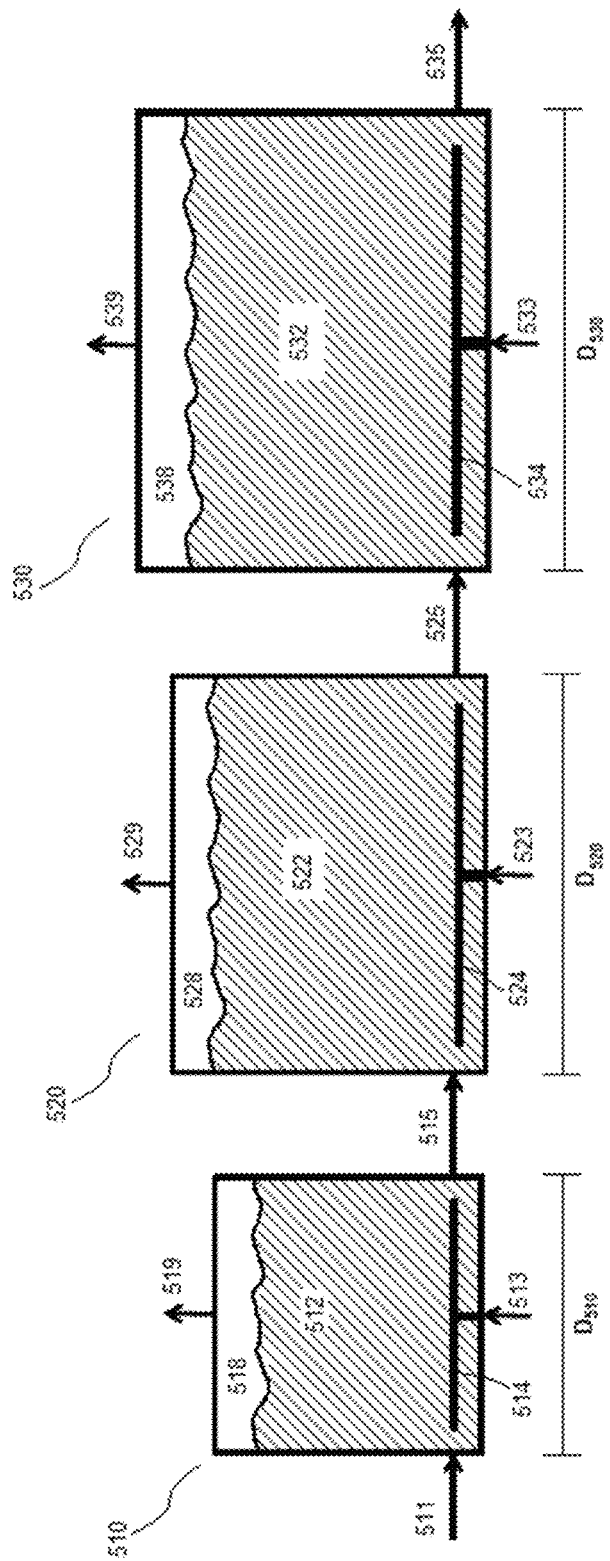
FIG. 5 is a diagram illustrating a reactor system in accordance with some aspects of the present invention.

Some embodiments furthermore provide a system of oxidation reactors, with at least one reactor having disposed therein a gas distributor according to the above description. Preferably, each oxidation reactor has such a gas distributor disposed therein. The reactors may be connected in series, as shown in FIG. 5 for a system comprising three oxidation reactors 510, 520, and 530. A first oxidation reaction mixture comprising cyclohexylbenzene is provided to the first oxidation reactor 510 as inlet stream 511 so as to form a first liquid-phase reaction medium 512 in the first oxidation reactor 510. An oxygen-containing gas is provided to the reactor 510 via first gas inlet 513 and distributed into the first liquid-phase reaction medium 512 via a first gas distributor 514 disposed in the first oxidation reactor 510 and in fluid communication with the first gas inlet 513. First gas overhead 518 in the first oxidation reactor 510 is drawn off as a first gas outlet stream 519. The oxygen concentration in the gas overhead 518 is maintained at 8 vol % or less, preferably 5 vol % or less.

The first oxidation reaction product, comprising an unreacted portion of the cyclohexylbenzene and cyclohexylbenzene-hydroperoxide product, exits as outlet stream 515, and is provided to the second oxidation reactor 520, which is in fluid communication with the first oxidation reactor 510 at least via stream 515. The first oxidation reaction product forms a second liquid-phase reaction medium 522 in the second oxidation reactor 520. Additional oxygen-containing gas is provided to the second oxidation reactor 520 via a second gas inlet stream 523, and distributed into the second liquid-phase reaction medium 522 via a second gas distributor 524 disposed in the second oxidation reactor 520 and in fluid communication with the second gas inlet 523. Second gas overhead 528 in the second oxidation reactor 520 is drawn off as a second gas outlet stream 529. The oxygen concentration in the gas overhead 528 is maintained at 8 vol % or less, preferably 5 vol % or less.

The second oxidation reaction product, comprising a remaining unreacted portion of the cyclohexylbenzene, the cyclohexylbenzene-hydroperoxide product, and additional cyclohexylbenzene-hydroperoxide product, exits as second outlet stream 525, and is provided to the third oxidation reactor 530, which is in fluid communication with the second oxidation reactor 520 at least via the second outlet stream 525. The second oxidation reaction product forms a third liquid-phase reaction medium 532 in the third oxidation reactor 530. Further additional oxygen-containing gas is provided to the third oxidation reactor 530 via a third gas inlet 533, and distributed into the third liquid-phase reaction medium 533 via a third gas distributor 534 disposed in the third oxidation reactor 530 and in fluid communication with the third gas inlet 533. A third gas overhead 538 forms and is drawn off as third gas outlet stream 539. The oxygen concentration in the third gas overhead 538 is maintained at under 10.5 vol %, preferably 8.5 vol % or less, such as 8.0 vol % or less, more preferably 5 vol % or less.

A third oxidation reaction product is formed in the third liquid-phase reaction medium 532 and removed as third outlet stream 535. This oxidation reaction product may comprise any remaining unreacted cyclohexylbenzene hydroperoxide, as well as the cyclohexylbenzene-hydroperoxide produced in each of the first and second oxidation reactors 510 and 520, and further cyclohexylbenzene hydroperoxide produced in the third oxidation reactor 530.

Modifications to the configuration of FIG. 5 are possible according to various embodiments. For instance, at least a portion of any one or more of the first, second, and third gas outlet streams 519, 529, and 539 may be recycled and/or reused so as to provide at least a portion of the oxygen-containing gas supplied to the first, second, and/or third reactor. Similarly, at least a portion of any one or more of the liquid outlet streams 515, 525, and 535 may be recycled to provide recycled reaction medium to one or more of the reactors 510, 520, and 530 (not shown in FIG. 5), either via an additional liquid inlet or by combination with the respective liquid inlet streams 511, 515, 525 for each reactor 510, 520, and 530. Such recycle streams may each include a suitable cooling device such as a heat exchanger so as to cool the liquid being returned to one or more of the reactors 510, 520, and 530. Furthermore, additional reactors (e.g., fourth, fifth, etc. oxidation reactors) may be connected in series in a like manner as described with respect to the first through third oxidation reactors. On the other hand, a series reactor system may comprise only two series oxidation reactors (e.g., only the first and second oxidation reactors 510 and 520).

Furthermore, as shown in FIG. 5, each oxidation reactor may have a different diameter. In particular, as per FIG. 5, the first, second, and third oxidation reactors 510, 520, and 530 may have progressively larger diameters $D_{510}$, $D_{520}$, and $D_{530}$, respectively. For instance, the first reactor diameter ($D_{510}$ in FIG. 5) may be from 35 to 45 feet (10.668 to 13.716 m); the second reactor diameter ($D_{520}$ in FIG. 5) may be from 50 to 70 feet (15.240 to 21.336 m); and the third reactor diameter ($D_{530}$ in FIG. 5) may be from 85 to 100 feet (25.908 to 30.480 m). Each gas distributor (514, 524, 534) may accordingly have progressively larger gas distributor cross-sectional areas (i.e., a first gas distributor horizontal cross-sectional area, a second gas distributor horizontal cross-sectional area larger than the first, and a third gas distributor horizontal cross-sectional area larger than the second) in order to maintain approximately equal gas distributor coverage in each reactor.

On the other hand, each reactor may have the same diameter (not shown in FIG. 5), or progressively smaller diameters (also not shown).

Figure 6:
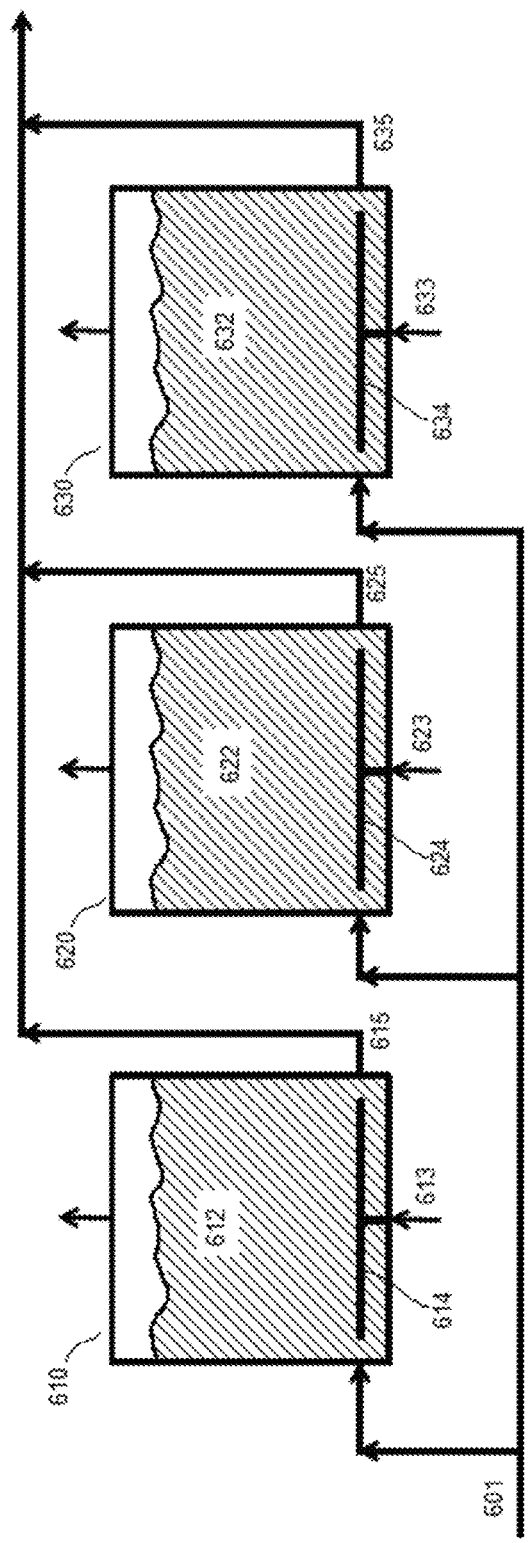
FIG. 6 is a diagram illustrating another reaction system in accordance with some aspects of the present invention.

Parallel reactor systems are also contemplated. For instance, as shown in FIG. 6, an oxidation reaction mixture comprising cyclohexylbenzene in stream 601 may be split and provided to each of three oxidation reactors 610, 620, and 630, forming therein first, second, and third liquid-phase reaction media 612, 622, and 632, respectively. Oxygen-containing gas is provided to each through gas inlets 613, 623, and 633, and distributed via gas distributors 614, 624, and 634, respectively. Each reactor produces a liquid-phase oxidation reaction product, withdrawn as product streams 615, 625, and 635, which may be combined as the product (as shown in FIG. 6). Alternatively (not shown in FIG. 6), at least a portion of any one or more product streams 615, 625, and 635 may be provided to one or more of the oxidation reactors 610, 620, 630 as additional oxidation reaction mixture (not shown in FIG. 6). As with series reaction systems, 2, 3, 4, 5, or more oxidation reactors in such parallel configuration are contemplated. Also as with series reaction systems, oxidation reactors in parallel configuration may have the same or differing diameters (shown in FIG. 6 with the same diameters). Further, various recycle streams (not shown in FIG. 6) may also be included in such reactor systems, such as recycle of at least a portion of the liquid outlet stream 615 to the first reactor 612 (either by combination with liquid inlet stream 601 or by delivery through an additional liquid inlet), or similar recycle of at least a portion of liquid outlet streams 625 and/or 635 to any one or more of the reactors 610, 620, 630. Such recycle streams may each include a suitable cooling device such as a heat exchanger so as to cool the liquid being returned to one or more of the reactors 610, 620, and 630.

Liquid Distribution

Theoretically, the liquid containing cyclohexylbenzene can be supplied into the oxidation reactor body via any port located anywhere on the reactor body wall. However, certain embodiments may also include a liquid distributor through which the oxidation reaction mixture is distributed into an oxidation reactor, forming the liquid-phase reaction medium in that reactor. Preferably, the liquid distributor is submerged in the liquid reaction medium during normal operation of the oxidation process. Any one or more oxidation reactors of a reactor system may include such a liquid distributor.

Where the reactor is equipped with both a liquid distributor and a gas distributor, the liquid distributor can be located, in part or in whole, below or above the gas distributor. Preferably, however, the liquid distributor is at least partly located above the gas distributor because this arrangement results in better agitation and mixing of the liquid reaction medium in the reactor body, improved contact between the gas phase and the liquid phase, and higher homogeneity of the reaction medium during normal operation where gas is supplied to the reaction medium. By "at least partly located above the gas distributor," it is meant that at least a portion of the liquid ingress ports through which liquid is delivered to the liquid phase reaction medium is/are located above at least a portion of the orifices on the gas distributor through which the gas enters the reaction medium. It is desired, however, that both the gas distributor and the liquid distributor are located in the lower portion of the reactor body.

To that end, if a liquid distributor is located completely above the gas distributor, it is desired that the distance between the highest orifice on the gas distributor and the lowest liquid ingress port on the liquid distributor is in a range from d1 meter(s) to d2 meter(s), where d1 and d2 can be, independently, 0.01, 0.02, 0.04, 0.05, 0.06, 0.08, 0.10, 0.15, 0.20, 0.25, 0.30, 0.35, 0.40, 0.45, 0.50, 0.55, 0.60, 0.65, 0.70, 0.80, 0.85, 0.90, 0.95, 1.0, 1.2, 1.4, 1.5, 1.6, 1.8, 2.0, as long as d1<d2.

An oxidation reactor or reactor system equipped with a liquid distributor may comprise components operable to withdraw and pump a portion of its contents through a suitable cooling device such as a heat exchanger and return the cooled portion to the reactor, thereby managing the heat release of the oxidation (of CHB) and decomposition (of CHB-HP) reactions. The recycle reaction medium stream may be combined with fresh cyclohexylbenzene stream before being delivered to a single liquid distributor. It is possible, however, that the fresh cyclohexylbenzene stream and the recycle reaction medium stream are supplied into the reactor body via separate liquid distributors, which may be of the same or different types, disposed inside the reactor body. Where multiple liquid distributors are present, both are preferably at least partly located above the gas distributor, as detailed above.

The amount of liquid, including the fresh cyclohexylbenzene feed and recycle reaction medium feed, to the reactor relative to the reactor volume depends on operating parameters, such as temperature, pressure, target conversion, and selectivity. The amount of recycle reaction medium relative to the amount of fresh cyclohexylbenzene liquid feed depends on the designed heat exchanger duty. The recycle ratio, defined as the weight ratio of the recycle reaction medium stream to the fresh cyclohexylbenzene stream, can range from r1 to r2, where r1 and r2 can be, independently, 0.1, 0.2, 0.4, 0.5, 0.6, 0.8, 1.0, 1.5, 2.0, 2.5, 3.0, 3.5, 4.0, 4.5, 5.0, 7.5, 10, 15, 20, 25, 30, 35, 40, 45, 50, 55, 60, 65, 70, 75, 80, as long as r1<r2.

In order to achieve the desired conversion and selectivity in the reactor while maintaining operational safety, good oxygen distribution and liquid mixing across the reactor cross-section is highly desired. The liquid distributor design can strongly influence the gas and liquid circulation and mixing of both gas and liquid species in the oxidation reactor. Moreover, the liquid distributor design desirably provides effective mixing in the reactor, either in the presence or in the absence of gas supply to ensure rapid and effective cool down of the reactor.

Preferably, the liquid distributor comprises a liquid-conveying conduit or a network of liquid-conveying conduits in direct or indirect fluid communication with one another, such that the liquid is distributed throughout the entire network of liquid-conveying conduits. The liquid distributor used for the oxidation reaction may be any type of liquid distributor that allows for introduction of liquid feed and/or recirculation streams to the reactor, and may further efficaciously provide contacting of oxygen and cyclohexylbenzene to effect the oxidation reaction. For example, the liquid distributor may be a perforated plate distributor, a porous plate distributor, a membrane distributor, a perforated pipe distributor, an arm-network distributor (similar to the gas distributor layout shown in FIG. 2), or a ring type distributor network comprising one ring conduit or multiple concentric ring conduits.

In some embodiments, the conduit or network of conduits of the liquid distributor are disposed within a "liquid distributor horizontal cross-sectional area" within a plane substantially parallel to the plane in which the gas distributor is disposed. The liquid distributor horizontal cross-sectional area is the smallest possible area within said horizontal plane that may be defined so as to encompass the network of liquid conduits. The horizontal plane in which the liquid distributor is disposed is furthermore preferably above the plane in which the gas distributor is disposed, such that the orifices of the gas distributor and the liquid ingress ports are spaced apart at any of the distances described previously. Furthermore, the liquid distributor horizontal cross-sectional area in some embodiments is from 50 to 100% of the cross-sectional area of the lower portion of the oxidation reactor in which the gas distributor is disposed (in other words, the "liquid distributor coverage," defined similarly to the gas distributor coverage, is from 50 to 100% of the cross-sectional area of the lower portion of the oxidation reactor in which the liquid distributor is disposed). Preferably, the liquid distributor coverage ranges from a low of any one of about 50, 55, 60, 65, 70, 75, 80, 85, 90, 95, 96, 98, and 99% to a high of any one of about 60, 65, 70, 75, 80, 85, 90, 95, 96, 98, 99, and 100%, provided the high end of the range is greater than the low end.

Preferably, the conduits of the liquid distributor have a plurality of liquid ingress ports (e.g., nozzles, jets, holes, or the like) disposed thereon, through which the liquid is delivered into the oxidation reactor, forming the liquid-phase reaction medium. In the course of normal operation, the conduits are submerged within the liquid-phase reaction medium, and deliver additional liquid to said reaction medium via the liquid ingress ports.

The conduits of the liquid distributor having the liquid ingress ports disposed thereon may have inner diameter within a range from a low of any one of about 0.01, 0.02, 0.03, 0.04, 0.05, 0.06, 0.07, 0.08, 0.09, and 0.10 meter, to a high of any one of about 0.06, 0.07, 0.08, 0.09, 0.10, 0.15, 0.20, 0.25, 0.30, 0.35, 0.40, 0.45, 0.50, 0.60, 0.70, 0.80, 0.90, and 1.0 meter. In some embodiments, the conduits have approximately equal (+/−5% from average) diameters. Alternatively, the conduits may have varying diameter. Typically, header conduits tend to have larger diameters than arm conduits in arm-network liquid distributors.

With respect to the liquid ingress ports on the liquid-conveying conduits, in some embodiments, there are on average 0.1 to 10 of the orifices per square foot (about 1.076 to 107.6 orifices per $m^2$) within the cross-sectional area in which the liquid ingress ports are located. Preferably, there are on average 0.5 to 5 liquid ingress ports per square foot (5.38 to 53.8 orifices per $m^2$); more preferably on average about 1 to 3 liquid ingress ports per square foot (about 10.76 to about 32.29 orifices per $m^2$), such as about 2 orifices per square foot (21.53 per $m^2$). Average distance between adjacent liquid ingress ports is about 0.05 to about 0.25 m. For instance, the distance between two adjacent liquid ingress ports may range from a low of any one of about 0.05, 0.06, 0.07, 0.08, 0.09, 0.1, 0.11, 0.12, 0.13, and 0.14 meter to a high of any one of about 0.10, 0.11, 0.12, 0.13, 0.14, 0.15, 0.16, 0.17, 0.18, 0.19, 0.20, and 0.25 meter, provided the high end of the range is greater than the low end.

Each liquid ingress port may have a diameter of about 1 mm to about 200 mm. Size of the liquid ingress ports can be determined according to the total flow rate and pressure of the cyclohexylbenzene-containing liquid supplied into the reactor body, the total number of the liquid ingress ports, and the like. Diameter of the liquid ingress port (defined as the diameter of the smallest circle that the inner cross-section of the liquid ingress port can fit into) may range from a low of any one of about 1, 2, 3, 4, 5, 10, 15, 20, 25, 30, 35, 40, 45, and 50 mm, to a high of any one of about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, and 200 mm, provided the high end of the range is greater than the low end. Thus, for instance, each liquid ingress port may have a diameter of about 15 to about 150 mm, such as about 50 to about 105 mm, etc.

The average liquid velocity per liquid ingress port may be between 0.1 and 100 m/s. Liquid ingress port velocity (or flow rate) may be important for mixing, particularly in the absence of gas supply. Therefore, it is preferred that the average liquid velocity per liquid ingress port is between 0.2 and 5 m/s. Depending on the liquid flow rate fed to the reactor, the desired liquid velocity per liquid ingress port also sets a design criteria for number of liquid ingress ports for the single ring-type distributor. The liquid distributor may be designed in a way that liquid ingress port velocities may be different, though it is preferred that they are the same.

Each liquid ingress port may be, e.g., a nozzle or other structure capable of directing the liquid flow in a particular orientation. The liquid ingress ports may be independently oriented in any of various directions. They may be stationary, enabling a fixed angle of the liquid stream ejected therefrom, or adjustable (movable), enabling changing angle of the liquid stream ejected therefrom. Each liquid ingress port may be oriented such that the liquid stream can be ejected upwards, downwards, toward the center of the reactor body, or away from the center of the reactor body. It is preferred that some are oriented at least partially towards the reactor walls while others are oriented away from the walls to mix the core of the reactor vessel. Further, it is also preferred that the ingress ports be oriented such that the liquid is ejected in a horizontal or at least partially upward direction within the reaction medium. That is, it is preferred to orient the liquid ingress ports at an orientation between that which is parallel to the reactor bottom (90°) and that pointing directly towards the reactor top (180°) (with 0° reference being oriented directly downward toward the reactor bottom).

The liquid distributor may contain any number of drainage holes through which liquid material can flow out of the distributor conduits due to gravity in case emptying the reactor body and/or the distributor conduits is needed. These drainage holes, where present, are in addition to, and not numbered as part of, the liquid ingress ports.

In some embodiments, as a result of liquid and/or gas distribution, good mixing of the reaction medium may lead to a low variation of temperature (Vt) of at most 10° C., 9° C., 8° C., 7° C., 6° C., 5° C., 4° C., 3° C., 2° C., or even 1° C., among the liquid medium at least 10 centimeters above the highest of the liquid distributor and the gas distributor. As used herein, variation of temperature (Vt) is defined as the difference between (a) the time-averaged temperature at a given location (Tloc) at least 10 centimeters above the highest of the liquid distributor and the gas distributor, and (b) the average (Tav) of the time-averaged temperatures of all liquid medium at least 10 centimeters above the liquid distributor:

$$Vt = |Tloc - Tav|.$$

Such low temperature variation means the minimization of hot spots within the liquid-phase reaction medium, which is especially desirable for suppressing undesirable side reactions, including but not limited to those involving decomposition of 1-CHB-HP, and the formation of other, undesirable cyclohexylbenzene hydroperoxides.

Where a reactor is equipped with a liquid distributor in addition to the gas distributor of some embodiments, during normal operation, liquid feeds including fresh cyclohexylbenzene feed and recycle reaction medium stream, are supplied to the reactor body as multiple jets forming part of the liquid reaction medium, and preferably the $O_2$-gas stream is bubbled through the gas distributor into the reaction medium. The kinetic energy entrained by the liquid streams and the gas bubbles causes agitation, mixing, and homogenization of the reaction medium inside the reactor body. During the operation of the overall process, there may be occasions where the gas supply is shut off, reduced in flow rate, accidentally or intentionally. At the beginning of the cut-off of gas supply, due to dissolved $O_2$ in the liquid phase, oxidation reactions continue, which may release heat. The reduced agitation as a result of loss of gas supply to the reaction medium could cause hot spot formation if the remaining agitation in the liquid medium was insufficient. Embodiments utilizing a liquid distributor in addition to the gas distributor could therefore advantageously ensure sufficient and proper agitation in the liquid-phase reaction medium even in such events where gas flow is stopped, and helps achieve a high homogeneity in concentrations and temperature distribution.

Supply of Cyclohexylbenzene to Oxidation Reaction

The cyclohexylbenzene supplied to the oxidation can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

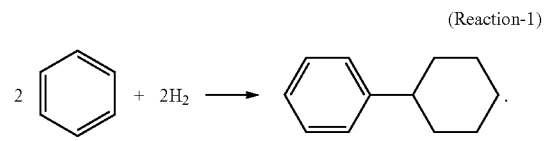 [SMILES: c1ccccc1 ; c1ccc(C2CCCCC2)cc1]

(Reaction-1)

Alternatively, cyclohexylbenzene can be produced by direct alkylation of benzene with cyclohexene in the presence of a solid-acid catalyst such as molecular sieves in the MCM-22 family according to the following Reaction-2:

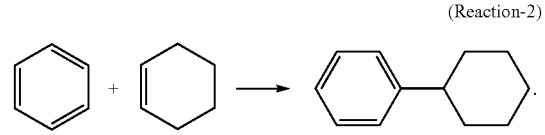

(Reaction-2)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 $hr^{-1}$ to 10 $hr^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

Cleavage of Cyclohexylbenzene-Hydroperoxide Resulting from Oxidation Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

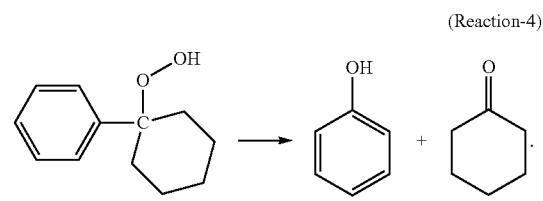 [SMILES: OOC1(c2ccccc2)CCCCC1 ; Oc1ccccc1 ; O=C1CCCCC1]

(Reaction-4)

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene. Acid catalysts preferably include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, sulfur trioxide, and solid acid catalysts such as zeolites. Sulfuric acid and solid acids are preferred acid catalysts.

The cleavage reaction can take place in a cleavage reactor in direct or indirect fluid communication with the oxidation reactor or the oxidation reactor system. The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10.

Separation and Purification

The cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first fractionation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., WIPO publications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent fractionation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

Other Gas-Liquid Oxidation Reactions

As noted previously, according to some embodiments, the processes, systems, and apparatus provided herein may be utilized in other gas-liquid oxidation reactions of liquid-phase organic reactants. Suitable examples include cumene oxidation to form cumene hydroperoxide, oxidation of cyclohexane to form cyclohexanol, and oxidation of anthrahydroquinone to form hydrogen peroxide, among others. Thus, in general, processes may include: providing a liquid phase feed comprising an oxidizable organic compound to an oxidation reactor, thereby forming a liquid-phase reaction medium in the oxidation reactor; providing an oxidation catalyst to the liquid-phase reaction medium; distributing an oxygen-containing gas into the liquid-phase reaction medium through a gas distributor; and forming an oxidized organic compound. The gas distributor may be in accordance with any of the embodiments previously described herein. Further, a reactor system as described herein may be used instead of a single oxidation reactor.

EXPERIMENTAL

The invention will now be more particularly described with reference to the following non-limiting Examples.

Example 1

Figure 7:
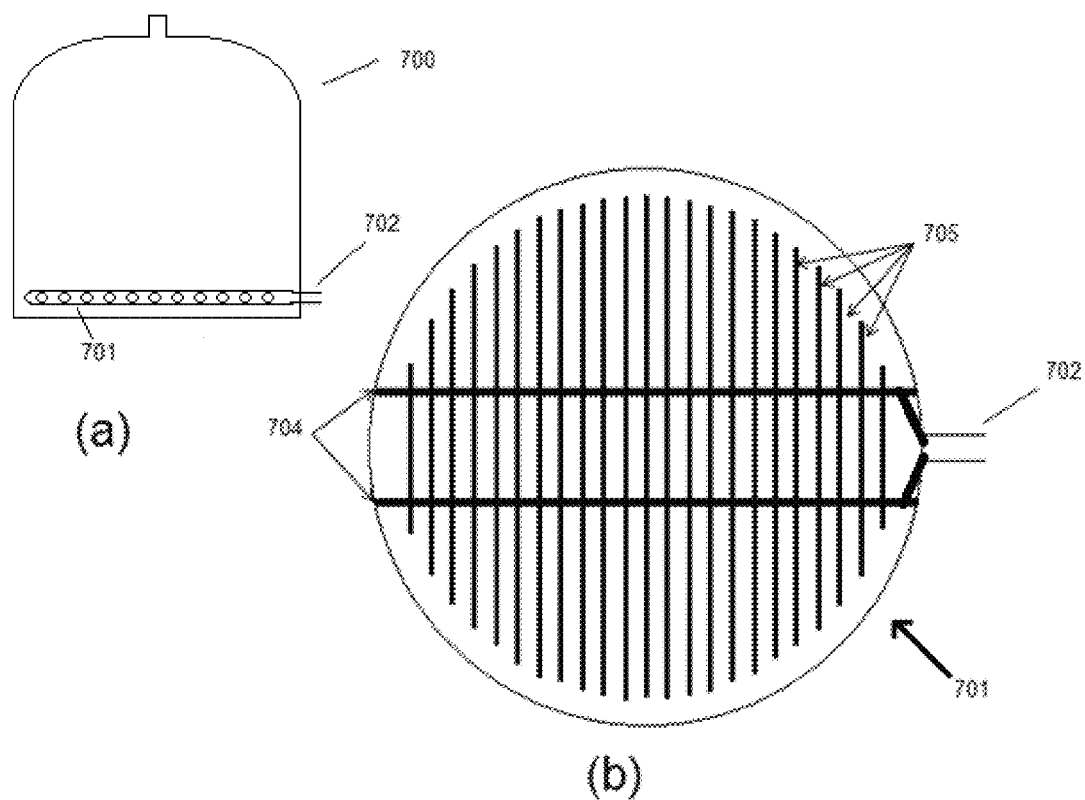
FIGS. 7(a) and 7(b) are side and plane view illustrations, respectively, of a gas distributor in an oxidation reactor according to Example 1.

An oxidation reactor 700 with an arm distributor network-type gas distributor 701 was designed according to the side view of FIG. 7(a) and plane view of FIG. 7(b), comprising 23 arm conduits 705 in fluid communication with (and running perpendicular to) two header conduits 704. Gas flow in the distributor was simulated using ANSYS Fluent CFD software. Gas flowing through inlet 702 was split and flowed into the two header conduits 704, through which the gas then flowed into the 23 arm conduits 705. The arm conduits 705 contained a plurality of nozzles disposed thereon (not shown in FIG. 7), through which the gas flow into a liquid-phase reaction medium in the reactor was simulated. The parameters of this gas distributor and oxidation reactor of Example 1 are given in Table 1.

TABLE 1

Example 1 Gas Distributor Parameters

|  | Unit | Value |
| --- | --- | --- |
| Reactor diameter | (m) | 14.95 |
| Unaerated liquid inventory height | (m) | 9.14 |

TABLE 1-continued

Example 1 Gas Distributor Parameters

| | Unit | Value |
|---|---|---|
| Total reactor height with overhead (approximate) | (m) | 14.5 |
| Gas feed rate | (kg/s) | 8.50 |
| Number of holes (approximate) | | 3061 |
| Nozzle orifice diameter | (mm) | 6 |
| Distributor Coverage | % | 81 |
| (Distributor distance from reactor side wall) | (m) | 0.75 |
| Nozzle orifice density | (1/ft$^2$) | 2 |
| Main header count | | 2 |
| Main header diameter | (m) | 0.25 |
| Spacing btw header pipes | (m) | 2.75 |
| Arm count | | 23 |
| Arm (section) diameter | (m) | 0.064 |
| Spacing between arms | (m) | 0.52 |
| Spacing between holes | (m) | 0.15 |
| Number of drainage holes | | 50 |
| Arm elevation (from reactor bottom) | (m) | 0.37 |
| Header elevation (from reactor bottom) | (m) | 0.28 |
| Nozzle orientation (from bottom) | ° | 45 |

Figure 8:
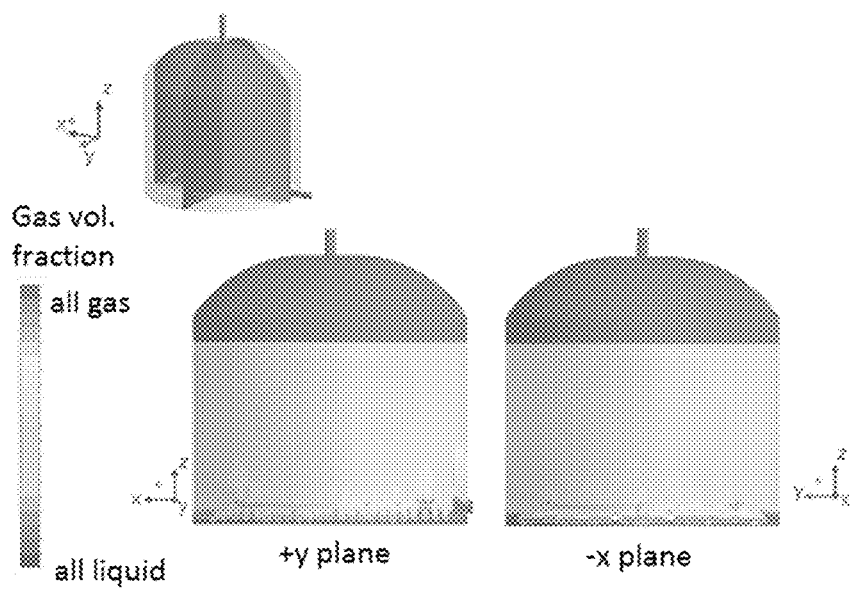
FIG. 8 is an illustration of a simulated distribution of oxygen-containing gas within a liquid-phase reaction medium in accordance with Example 1.

The computational fluid dynamic simulation of the Example 1 gas distributor yielded a nearly uniform distribution of gas through the liquid-phase reaction medium, as shown in FIG. 8. In particular, FIG. 8 shows the time-averaged gas volume fraction (holdup) profiles at two vertical planes within the oxidation reactor: one plane having a normal oriented in the +y direction and the other plane having a normal oriented in the −x direction, as shown in FIG. 8. The average gas oxygen mol fraction in the overhead in this simulated reactor was maintained at about 0.08. All oxygen mol fractions in the overhead were well below the 0.105 mol fraction limit of safe operation for this system.

Example 2

Figure 9:
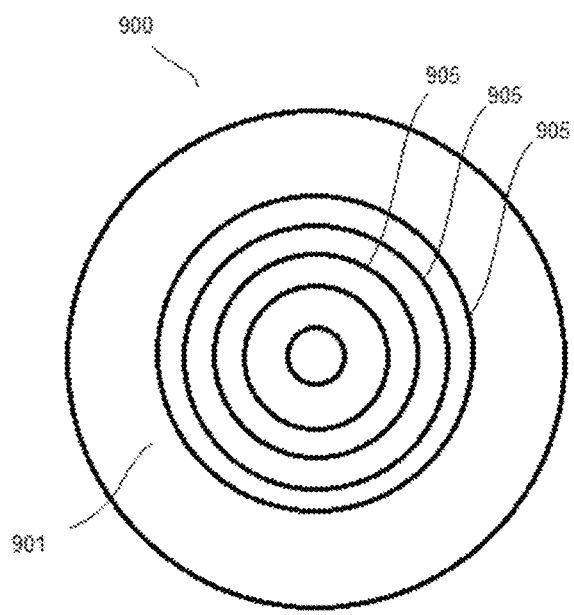
FIG. 9 is a plane view of a gas distributor in accordance with Example 2.

A similar simulation was run for an oxidation reactor having the same parameters, and with a gas distributor having similar orifice sizes, orifice density, elevation, and spacing. However, instead of the arm distributor network-type distributor of Example 1, the distributor of Example 2 is a concentric ring-type distributor. More importantly, distributor coverage in Example 2 is only 50% of the reactor cross-section, as compared to the 81% of Example 1. FIG. 9 shows a plane view of the Example 2 gas distributor 901, having a plurality of ring conduits 905 disposed within the reactor 900.

Figure 10:
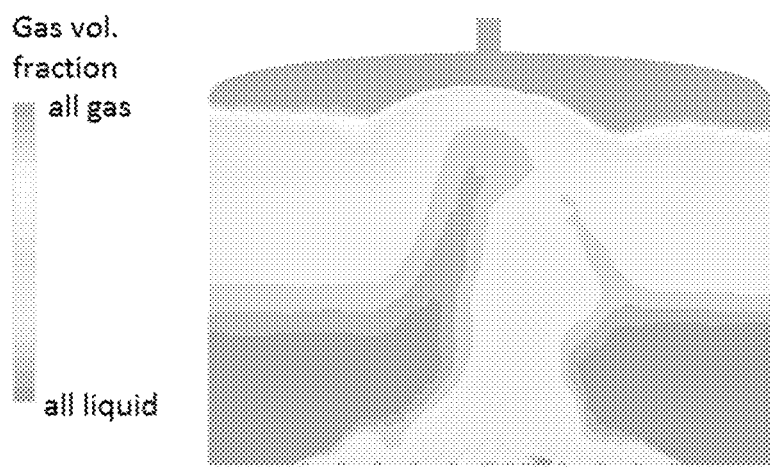
FIG. 10 is an illustration of a simulated distribution of oxygen-containing gas within a liquid-phase reaction medium in accordance with Example 2.

As shown in FIG. 10, the simulated distribution of the gas into the liquid-phase reaction medium resulted in a far less uniform gas distribution as compared to the distributor of Example 1.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including." Whenever a composition, an element or a group of elements is preceded with the transitional phrase "comprising," it is understood that—unless the context plainly dictates otherwise—we also contemplate the same composition or group of elements with transitional phrases "consisting essentially of," "consisting of," "selected from the group consisting of," or "is" preceding the recitation of the composition, element, or elements and vice versa.

We claim:

1. A process comprising:
    (a) providing a liquid feed comprising cyclohexylbenzene to an oxidation reactor, thereby forming a liquid-phase reaction medium in the oxidation reactor;
    (b) providing an oxidation catalyst to the liquid-phase reaction medium, either together with or separately from the liquid feed;
    (c) distributing an oxygen-containing gas into the liquid-phase reaction medium through a gas distributor, wherein the gas distributor (i) is disposed in a lower portion of the oxidation reactor, (ii) is submerged in the liquid-phase reaction medium, and (iii) comprises a network of conduits through which the oxygen-containing gas flows, said conduits being in direct or indirect fluid communication with one another and having disposed thereon a plurality of orifices through which the oxygen-containing gas passes from the conduits into the liquid-phase reaction medium; and
    (d) forming cyclohexylbenzene hydroperoxide in the liquid-phase reaction medium;
    wherein the conduits are disposed within a gas distributor horizontal cross-sectional area that is substantially parallel to a bottom surface of the oxidation reactor, and which occupies from 70 to 95% of the cross sectional area of the lower portion of the oxidation reactor in which the gas distributor is disposed; and
    wherein there are on average 0.5-5 of the orifices per square foot within the gas distributor horizontal cross-sectional area.

2. The process of claim 1, wherein the orifices are nozzles.

3. The process of claim 2, wherein each nozzle is oriented such that the oxygen-containing gas exits the nozzle in (i) a direction within the plane of the distributor horizontal cross sectional area, (ii) a direction perpendicular to the distributor horizontal cross sectional area and toward a bottom of the oxidation reactor, or (iii) a direction at any angle therebetween.

4. The process of claim 1, wherein the oxygen-containing gas, after being passed through the orifices, contacts the bottom of the oxidation reactor at least in part, and thereafter rises upward through the liquid phase reaction medium as a plurality of bubbles.

5. The process of claim 1, wherein there are on average 1 to 2 of the orifices per square foot within the distributor horizontal cross sectional area.

6. The process of claim 1, wherein each orifice through which the oxygen-containing gas flows is 3 to 6 mm in diameter.

7. The process of claim 1, wherein the network of conduits is an arm distributor network comprising (i) 1 to 5 header conduits running parallel to each other through the distributor cross sectional area and (ii) 10 to 50 arm conduits each in fluid communication with at least one of the header conduits, and running through the distributor horizontal cross sectional area in a direction transverse to the header conduits.

8. The process of claim 7, wherein the arm conduits each run substantially perpendicular to the header conduit(s).

9. The process of claim 7, wherein the arm distributor network comprises (i) 2 header conduits running substantially parallel to each other and (ii) 23 arm conduits, each arm conduit being in fluid communication with both header conduits, and each arm conduit running substantially perpendicular to the header conduits.

10. The process of claim 1, wherein the oxygen-containing gas is delivered to the liquid-phase reaction medium such that in any given continuous area of 10.0 centimeters by 10.0 centimeters inside (i) a first horizontal cross-section of the liquid-phase reaction medium 100 centimeters above the gas distributor, and/or (ii) a second horizontal cross-section of the liquid-phase reaction medium 500 centimeters above the gas distributor, the average quantity of oxygen passing through the given continuous area per second QO1 is in a range from 60% to 140% of QO2, where QO2 is the average quantity of oxygen passing through the whole given horizontal cross-section, expressed in terms of quantity of oxygen per 100 square centimeters per second.

11. The process of claim 10, wherein the time-averaged gas volume fraction through the entirety of each of the first and second horizontal cross-sections of the liquid-phase reaction medium is less than 0.130 during the distributing (c); and further wherein the oxygen concentration in a vapor-phase headspace in the reactor above the liquid-phase reaction medium remains at or below 8 vol % during the distributing (c).

12. The process of claim 1, wherein the oxidation reactor is a cylinder of average diameter D centered upon a reactor vertical axis, and further wherein the distributor horizontal cross-sectional area is centered upon the reactor vertical axis.

13. The process of claim 12, wherein the average diameter D is from 35 ft (10.668 m) to 100 ft (30.480 m).

14. The process of claim 13, wherein the average diameter D is from 35 ft (10.668 m) to 50 ft (15.240 m); and wherein the process further comprises:
(e) obtaining a first oxidation effluent comprising the cyclohexylbenzene hydroperoxide and unreacted cyclohexylbenzene from the liquid-phase reaction medium;
(f) providing the first oxidation effluent and additional oxidation catalyst to a second oxidation reactor having diameter D2 from 50 ft (15.240 m) to 70 ft (21.336 m), forming therein a second liquid-phase reaction medium;
(g) distributing additional oxygen-containing gas into the second liquid-phase reaction medium through a second gas distributor, wherein the second gas distributor (i) is disposed in a lower portion of the second oxidation reactor, (ii) is submerged in the second liquid-phase reaction medium, and (iii) comprises a network of additional conduits through which the additional oxygen-containing gas flows, said additional conduits being in direct or indirect fluid communication with one another and having disposed thereon a plurality of additional orifices through which the additional oxygen-containing gas passes from the additional conduits into the second liquid-phase reaction medium; and
(h) forming additional cyclohexylbenzene hydroperoxide in the second liquid-phase reaction medium;
wherein the additional conduits run substantially parallel to, and are disposed within, a second distributor horizontal cross-sectional area that is from 70 to 95% of the cross sectional area of the lower portion of the second oxidation reactor in which the second gas distributor is disposed; and
wherein there are on average 0.5-5 of the additional orifices per square foot within the second distributor horizontal cross sectional area.

15. The process of claim 14, and further comprising:
(i) obtaining a second oxidation effluent comprising the cyclohexylbenzene hydroperoxide, the additional cyclohexylbenzene hydroperoxide, and a portion of the unreacted cyclohexylbenzene from the second liquid-phase reaction medium;
(j) providing the second oxidation effluent and further oxidation catalyst to a third oxidation reactor having diameter D3 from 85 ft (25.908 m) to 100 ft (30.480 m), forming therein a third liquid-phase reaction medium;
(k) distributing further oxygen-containing gas into the third liquid-phase reaction medium through a third gas distributor, wherein the third gas distributor (i) is disposed in a lower portion of the third oxidation reactor, (ii) is submerged in the third liquid-phase reaction medium, and (iii) comprises a network of further conduits through which the further oxygen-containing gas flows, said further conduits being in direct or indirect fluid communication with one another and having disposed thereon a plurality of further orifices through which the further oxygen-containing gas passes from the further conduits into the third liquid-phase reaction medium; and
(l) forming further cyclohexylbenzene hydroperoxide in the third liquid-phase reaction medium;
wherein the further conduits run substantially parallel to, and are disposed within, a third distributor horizontal cross-sectional area that is from 70 to 95% of the cross sectional area of the lower portion of the third oxidation reactor in which the third gas distributor is disposed; and
wherein there are on average 0.5-5 of the further orifices per square foot within the third distributor horizontal cross sectional area.

16. The process of claim 1, wherein the oxidation catalyst is an N-hydroxy-substituted cyclic imide.

17. The process of claim 1, wherein the liquid feed is provided to the oxidation reactor through a liquid distributor, wherein the liquid distributor comprises a conduit or a network of conduits in direct or indirect fluid communication with one another, the conduit or conduits having disposed thereon a plurality of liquid ingress ports through which the liquid feed is provided to the oxidation reactor, and further
wherein the liquid distributor is disposed in the lower portion of the oxidation reactor and at least partially located above the gas distributor.

18. A reactor system comprising:
(I) a first oxidation reactor having disposed thereon (i) a first liquid inlet configured to receive a liquid-phase oxidation reaction mixture, such that a first liquid-phase reaction medium is formed in the first oxidation reactor as the liquid-phase oxidation reaction mixture is received through the first liquid inlet during operation of the reactor system; (ii) a first gas inlet configured to receive an oxygen-containing gas; (iii) a first liquid outlet through which a first oxidation reaction product may flow from the first liquid-phase reaction medium; and
(I-a) a first gas distributor disposed in a lower portion of the first oxidation reactor and further in fluid communication with the first gas inlet, wherein
(i) the first gas distributor comprises a first network of conduits, said conduits being in direct or indirect fluid communication with one another such that the oxygen-containing gas received by the first gas inlet during operation of the reactor system flows through the entire network of conduits, and said conduits having disposed thereon a first plurality of orifices through which the oxygen-containing gas may flow out of the first gas distributor and into the first liquid-phase reaction medium;

(ii) the conduits of the first gas distributor are disposed within a first gas distributor horizontal cross-sectional area that is substantially parallel to a bottom surface of the first oxidation reactor, and which occupies from 70 to 95% of the cross sectional area of the lower portion of the first oxidation reactor in which the first gas distributor is disposed; and (iii) there are on average 0.5-5 of the orifices per square foot within the first gas distributor horizontal cross-sectional area.

19. The reactor system of claim 18, further comprising:
(II) a second oxidation reactor having disposed thereon (i) a second liquid inlet configured to receive at least a portion of the first oxidation reaction product from the first oxidation reactor, such that the second oxidation reactor is in fluid communication with the first oxidation reactor via the first liquid outlet and the second liquid inlet, and such that a second liquid-phase reaction medium is formed in the second oxidation reactor as the first oxidation reaction product is received through the second liquid inlet during operation of the reactor system; (ii) a second gas inlet configured to receive additional oxygen-containing gas; and (iii) a second liquid outlet through which a second oxidation reaction product may flow from the second liquid-phase reaction medium; and (II-a) a second gas distributor disposed in a lower portion of the second oxidation reactor and further in fluid communication with the second gas inlet, wherein
(i) the second gas distributor comprises a second network of conduits, said conduits of the second gas distributor being in direct or indirect fluid communication with one another such that the additional oxygen-containing gas received by the second gas inlet during operation of the reactor system flows through the entire second network of conduits, and said conduits of the second gas distributor having disposed thereon a second plurality of orifices through which the additional oxygen-containing gas may flow out of the second gas distributor and into the second liquid-phase reaction medium;
(ii) the conduits of the second gas distributor are disposed within a second gas distributor horizontal cross-sectional area that is substantially parallel to a bottom surface of the second oxidation reactor, and which occupies from 70 to 95% of the cross sectional area of the lower portion of the second oxidation reactor in which the second gas distributor is disposed; and
(iii) there are on average 0.5-5 of the orifices per square foot within the second gas distributor horizontal cross-sectional area.

20. The reactor system of claim 19, further comprising:
(III) a third oxidation reactor having disposed thereon (i) a third liquid inlet configured to receive at least a portion of the second oxidation reaction product from the second oxidation reactor, such that the third oxidation reactor is in fluid communication with the second oxidation reactor via the second liquid outlet and the third liquid inlet, and such that a third liquid-phase reaction medium is formed in the second oxidation reactor as the second oxidation reaction product is received through the third liquid inlet during operation of the reactor system; (ii) a third gas inlet configured to receive additional oxygen-containing gas; and (iii) a third liquid outlet through which a third oxidation reaction product may flow from the third liquid-phase reaction medium; and (III-a) a third gas distributor disposed in a lower portion of the third oxidation reactor and further in fluid communication with the third gas inlet, wherein
(i) the third gas distributor comprises a third network of conduits, said conduits of the third gas distributor being in direct or indirect fluid communication with one another such that the further oxygen-containing gas received by the second gas inlet during operation of the reactor system flows through the entire third network of conduits, and said conduits of the third gas distributor having disposed thereon a third plurality of orifices through which the further oxygen-containing gas may flow out of the third gas distributor and into the third liquid-phase reaction medium;
(ii) the conduits of the third gas distributor are disposed within a third gas distributor horizontal cross-sectional area that is substantially parallel to a bottom surface of the third oxidation reactor, and which occupies from 70 to 95% of the cross sectional area of the lower portion of the third oxidation reactor in which the second gas distributor is disposed; and
(iii) there are on average 0.5-5 of the orifices per square foot within the third gas distributor horizontal cross-sectional area.

21. The reactor system of claim 20, wherein the first, second, and third oxidation reactors are each cylinders having respective diameters D1, D2, and D3, such that D3>D2>D1.

22. The reactor system of claim 21, wherein D1 is from 35 ft (10.668 m) to 50 ft (15.240 m); D2 is from 50 ft (15.240 m) to 70 ft (21.336 m); and D3 is from 85 ft (25.908 m) to 100 ft (30.480 m).

23. The reactor system of claim 18, wherein each of the orifices are nozzles oriented at an angle between −90° and +90°, where 0° is a vector pointing directly at a bottom surface of the reactor in which each orifice is disposed.

24. The reactor system of claim 20, wherein there are on average 1 to 2 of the orifices per square foot within each of the first, second, and third gas distributor horizontal cross-sectional areas.

25. The reactor system of claim 20, wherein:
(A) the first oxidation reactor further comprises a first liquid distributor comprising a conduit or a network of conduits in direct or indirect fluid communication with one another, the conduit or conduits having disposed thereon a first plurality of liquid ingress ports,
wherein the first liquid distributor is in fluid communication with the first liquid inlet such that the liquid-phase oxidation reaction mixture received by the first liquid inlet during operation of the reactor system flows through the first liquid distributor and out of the first plurality of liquid ingress ports into the first oxidation reactor; and further
wherein the first liquid distributor is disposed in the lower portion of the first oxidation reactor and at least partially located above the first gas distributor;

(B) the second oxidation reactor further comprises a second liquid distributor comprising a conduit or a network of conduits in direct or indirect fluid communication with one another, the conduit or conduits having disposed thereon a second plurality of liquid ingress ports,
- wherein the second liquid distributor is in fluid communication with the second liquid inlet such that the first oxidation reaction product received by the second liquid inlet during operation of the reactor system flows through the second liquid distributor and out of the second plurality of liquid ingress ports into the second oxidation reactor; and further
- wherein the second liquid distributor is disposed in the lower portion of the second oxidation reactor and at least partially located above the second gas distributor; and (C) the third oxidation reactor further comprises a third liquid distributor comprising a conduit or a network of conduits in direct or indirect fluid communication with one another, the conduit or conduits having disposed thereon a third plurality of liquid ingress ports,
- wherein the third liquid distributor is in fluid communication with the third liquid inlet such that the second oxidation reaction product received by the third liquid inlet during operation of the reactor system flows through the third liquid distributor and out of the third plurality of liquid ingress ports into the third oxidation reactor; and further
- wherein the third liquid distributor is disposed in the lower portion of the third oxidation reactor and at least partially located above the third gas distributor.

* * * * *